United States Patent
Liberatore et al.

(10) Patent No.: US 7,500,385 B2
(45) Date of Patent: Mar. 10, 2009

(54) SYSTEM FOR IN-SITU OPTICAL MEASUREMENT AND SAMPLE HEATING DURING RHEOMETRIC MEASUREMENTS

(75) Inventors: Matthew Liberatore, Arvada, CO (US); Norman Wagner, Newark, DE (US); Peter Foster, Lingfield (GB)

(73) Assignees: Waters Investments Limited, New Castle, DE (US); University of Delaware, Newark, DE (US)

(*) Notice: Subject to any disclaimer, the term of this patent is extended or adjusted under 35 U.S.C. 154(b) by 219 days.

(21) Appl. No.: 11/603,086

(22) Filed: Nov. 22, 2006

(65) Prior Publication Data
US 2007/0266776 A1 Nov. 22, 2007

Related U.S. Application Data

(60) Provisional application No. 60/741,869, filed on Dec. 5, 2005, provisional application No. 60/739,011, filed on Nov. 23, 2005.

(51) Int. Cl.
*G01N 11/00* (2006.01)

(52) U.S. Cl. .................................................. 73/54.23

(58) Field of Classification Search ............... 73/54.23, 73/54.27, 54.29, 54.33, 54.39; 356/72
See application file for complete search history.

(56) References Cited

U.S. PATENT DOCUMENTS

| | | | | |
|---|---|---|---|---|
| 4,602,501 A | * | 7/1986 | Hirata | 73/54.23 |
| 4,763,512 A | * | 8/1988 | Taylor | 73/54.27 |
| 5,040,410 A | * | 8/1991 | Chu et al. | 73/54.01 |
| 5,151,748 A | * | 9/1992 | Bur et al. | 356/32 |
| 5,327,778 A | * | 7/1994 | Park | 73/54.21 |
| 6,484,567 B1 | * | 11/2002 | Hajduk et al. | 73/54.37 |
| 2002/0116987 A1 | * | 8/2002 | Braithwaite et al. | 73/54.01 |
| 2007/0266776 A1 | * | 11/2007 | Liberatore et al. | 73/54.23 |
| 2008/0047328 A1 | * | 2/2008 | Wang | 73/54.39 |

OTHER PUBLICATIONS

Fuller, Gerald (1995). *Optical Rheometry of Complex Fluids.* New York, NY: Oxford University Press. pp. 52-76, 149-180, 181-192.

(Continued)

*Primary Examiner*—John Fitzgerald
(74) *Attorney, Agent, or Firm*—Aslan Baghdadi; Paul, Hastings, Janofsky & Walker LLP

(57) ABSTRACT

An optical rheometer system includes a rheometer chamber that can retain a fluid sample to be measured. A light source is provided that creates a light beam incident on the fluid sample. A Peltier heating plate is provided that has a channel region located within the plate. The channel region is configured to substantially transmit a light beam emitted from the light source and incident on the Peltier heating plate. In one embodiment, a rotating optical plate is provided opposed to a first surface of the Peltier plate. The rotating optical plate is substantially transparent such that light from a light beam emerging from the channel region of the Peltier plate can pass through the optical plate and be recorded at a detector. Peltier elements in the Peltier heating plate are arranged to provide uniform heating of sample fluid located on the first surface of the Peltier heating plate. The Peltier elements are further arranged to permit light to pass through the channel substantially unattenuated.

20 Claims, 6 Drawing Sheets

OTHER PUBLICATIONS

Liberatore, M., & McHugh, A. (2005). Dynamics of shear-induced structure formation in high molecular weight aqueous solutions. *Journal of Non-Newtonian Fluid Mechanics. 132*, 45-52.

van Egmond, J., Werner, D., & Fuller, G. (1992). Time-dependent small-angle light scattering of shear-induced concentration fluctuations in polymer solutions. *J. Chem. Phys. 96*, 7742-7757.

* cited by examiner

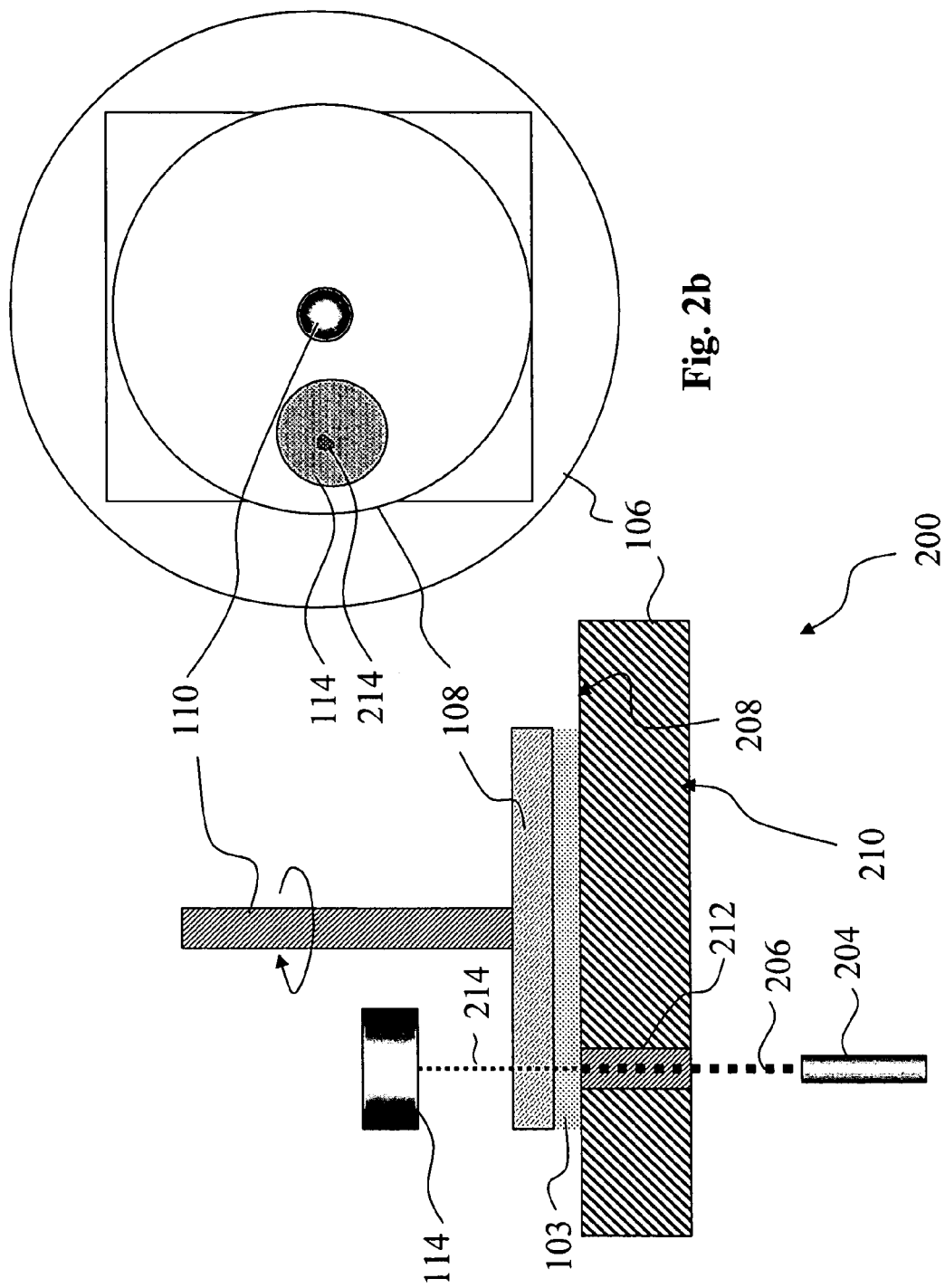

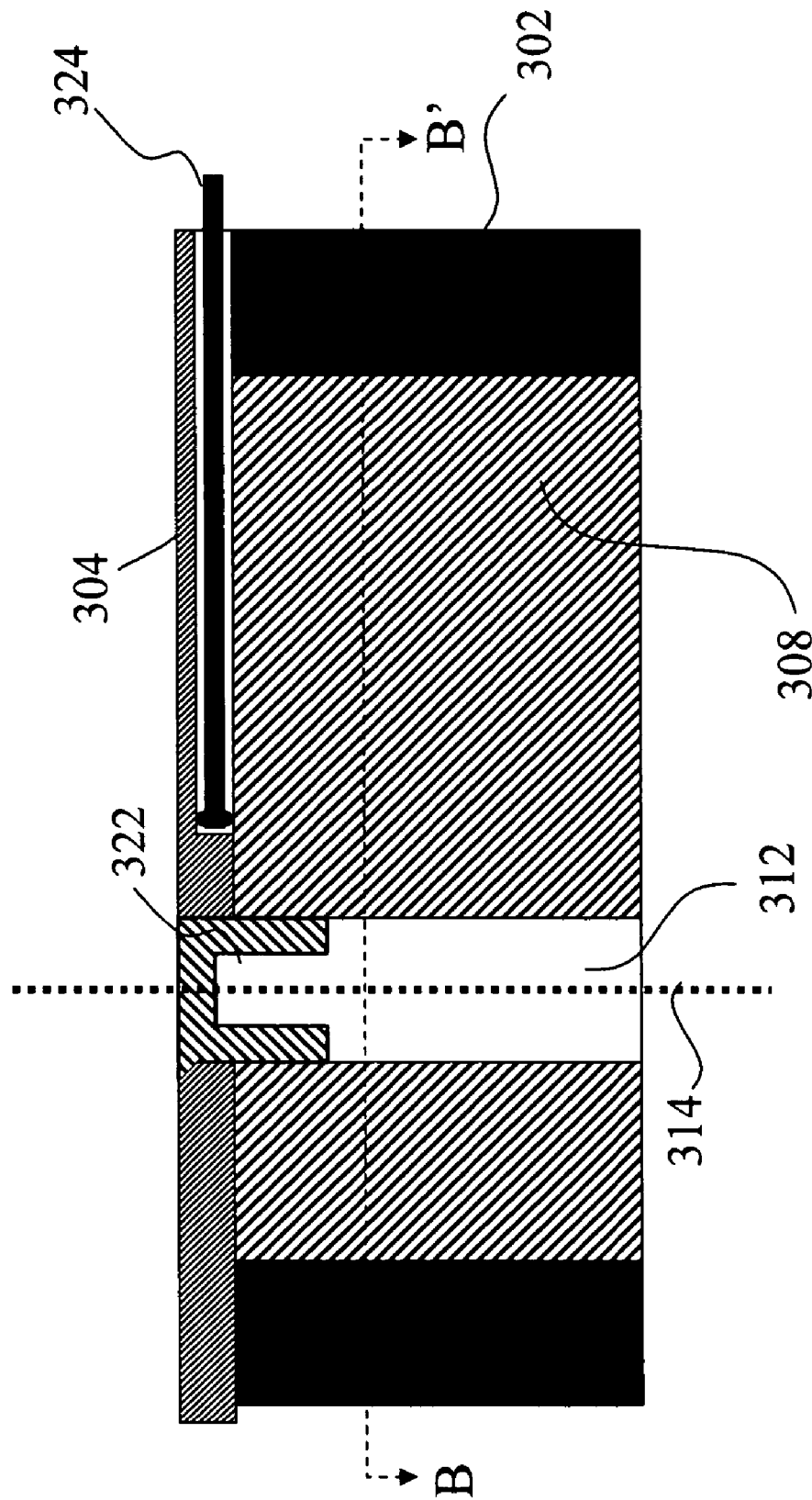

SYSTEM FOR IN-SITU OPTICAL MEASUREMENT AND SAMPLE HEATING DURING RHEOMETRIC MEASUREMENTS

This application claims priority to U.S. Provisional Patent Application No. 60/739,011, filed Nov. 23, 2005, and to U.S. Provisional Patent Application No. 60/741,869, filed Dec. 5, 2005, both of which are incorporated by reference herein in their entirety.

BACKGROUND

1. Field of the Invention

The, present invention relates generally to rheology and in particular to improvements in optical rheometric testing.

2. Background of the Invention

In the rheology field the control of temperature of a sample under test is important because of the temperature sensitivity of properties such as viscoelastic behavior. In one known configuration, a sample is located between an upper and lower plate as illustrated in FIG. 1a. System 10 of FIG. 1a includes an upper rotatable plate 12 and a lower fixed plate 14. Upper plate 12 is configured to introduce a shear strain/stress into a fluid sample 13 in contact with plate 12 during plate rotation or oscillation. By simultaneous heating of the fluid sample the fluid rheological behavior can be studied as a function of temperature.

Many methods of fluid sample heating are known, such as forced convection, radiant heating, direct resistive heating of a lower plate, direct Peltier heating of a lower plate, and so forth. Each heating method when used in conjunction with rheometry has drawbacks due to limitations imposed by the specific apparatus used for heating, among other factors. For example, forced convection can introduce mechanical disturbances into the fluid sample under study. Radiant heating can introduce temperature gradients that make fluid temperature hard to control. Direct resistive heating of a lower plate and Peltier heating typically involve opaque metallic elements that preclude use of fluid sample optical measurements during rheometric measurements. For example, in known rheometers, a rotating plate, such as upper plate 12, can be fabricated using an optically transparent material to facilitate optical measurements of a sample fluid using an optical probe that passes through the sample and plate. However, if lower plate 14 is a heating plate that heats a sample placed above it using resistive or Peltier heating, plate 14 will block light so that an optical probe cannot easily access a heated fluid sample near plate 14. Accordingly, known rheometer systems in which sample heating is employed are limited in terms of measurement flexibility and control.

BRIEF SUMMARY OF THE INVENTION

In one embodiment of the present invention, an optical rheometer system includes a rheometer chamber than can retain a fluid sample to be measured. As used herein, the term "rheometer" encompasses instruments also referred to as viscometers or viscosimeters. A light source is provided that creates a light beam incident on the fluid sample. Preferably, the beam is arranged to pass through the fluid sample so that light from the transmitted beam can be conveniently detected. A Peltier heating plate is provided that has a channel region located within the heating plate. The channel region is configured to substantially transmit a light beam emitted from the light source and incident on the Peltier heating plate. In one embodiment, a rotating optical plate is provided opposed to a first surface of the Peltier plate. The rotating optical plate is substantially transparent such that light from a light beam emerging from the channel region of the Peltier plate can pass through the optical plate and be recorded at a detector. Peltier elements in the Peltier heating plate are arranged to provide uniform heating of sample fluid located on the first surface of the Peltier heating plate. The Peltier elements are further arranged to permit light to pass through the channel region with relatively low attenuation. Accordingly, accurate fluid sample heating and temperature measurement can be performed simultaneously with optical measurements on a fluid subjected to stresses and strains imparted by the rotating optical plate.

In another embodiment of the present invention, a system for improved in-situ temperature control and optical measurements of a sample fluid includes a Peltier heating plate upon which sample fluid can be placed. The Peltier heating plate is capable of heating and maintaining a temperature to an accuracy of about 0.1-0.01° C. The system further includes an arrangement of Peltier heating elements that provide substantial heating uniformity across a first surface of the Peltier heating plate. The Peltier heating elements are separated by a border region that contains an optical channel disposed across the Peltier plate thickness that provides a path for visible light incident on the Peltier plate to travel through. The system further includes a light source that provides a laser beam incident on the Peltier heating plate on a side opposite to the first surface at a position and angle wherein a substantial fraction of the laser beam is transmitted through the Peltier plate. The channel includes a transparent window portion having an outer surface that is substantially flush with the first surface of the Peltier heating plate. The system further includes a detector disposed opposing the first surface of the Peltier heating plate. Accordingly, in-situ heating of a fluid sample can be performed with 0.1-0.01° C. control while performing optical measurements of the sample fluid using the laser beam.

BRIEF DESCRIPTION OF THE DRAWINGS

FIGS. 2a and 2b depict side cross-sectional and top views, respectively, of a multimeasurement system arranged in accordance with another embodiment of the present invention.

FIGS. 3a, 3b, and 3c depict, in a top view (FIG. 3a) and cross-sectional side views (FIGS. 3b and 3c), respectively, details of a Peltier heating plate arranged according to an embodiment of the present invention.

DETAILED DESCRIPTION OF THE INVENTION

Figure 1A:
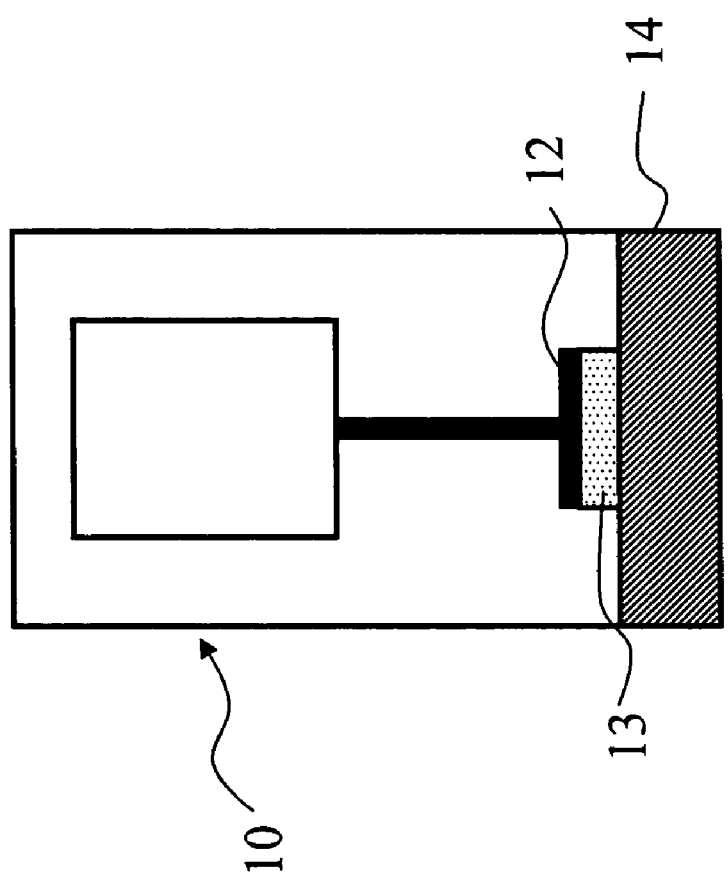
FIG. 1a depicts a known rheometer arrangement.
Figure 1B:
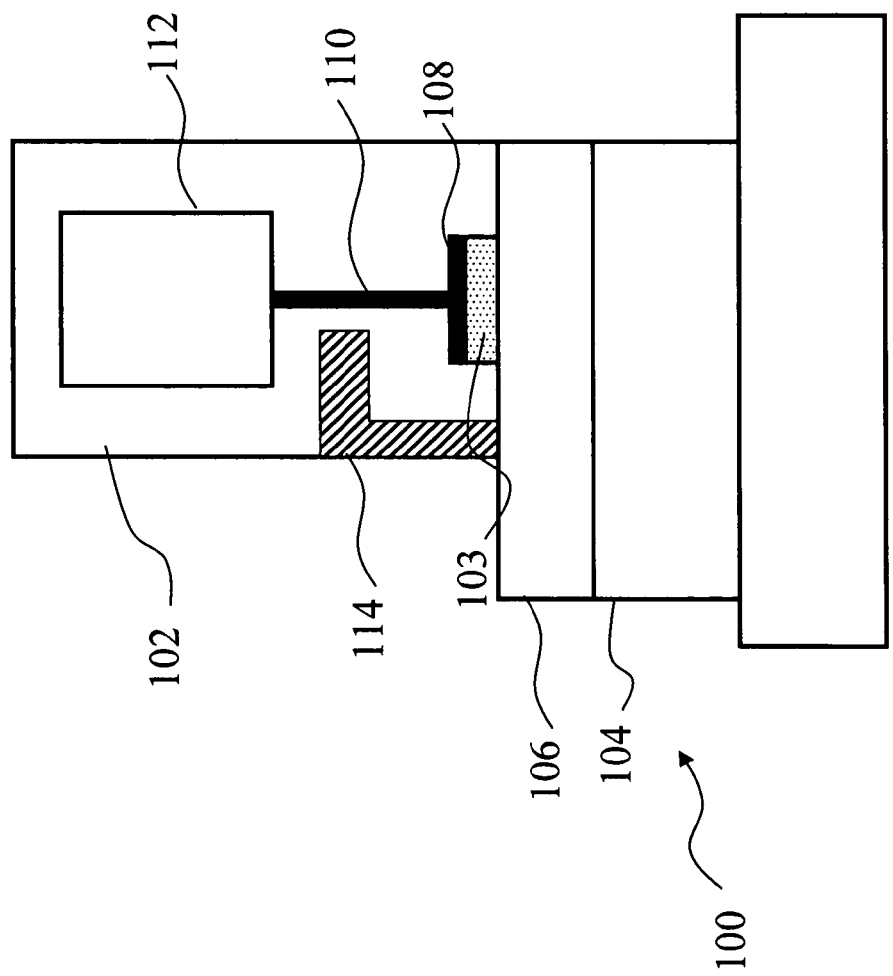
FIG. 1b illustrates general features of a system for in-situ optical measurements during sample heating of a fluid sample, according to an embodiment of the present invention.

FIG. 1b illustrates general features of a system 100 for in-situ optical measurements during sample heating of a fluid sample, according to an embodiment of the present invention. System 100 includes a rheometer chamber 102 that can house a fluid sample 103 that is typically disposed in a lower portion of the chamber. System 100 further includes light source 104 that directs a light beam such that it is incident on chamber 102, as well as a Peltier heating plate 106 used to heat sample fluid 103. Optical plate 108 is configured to rotate or oscillate when rotating shaft 110 is driven by motor 112. When optical plate 108 rotates or oscillates, a shear can be introduced into fluid sample 103 and viscolelastic properties of the fluid measured. Use of Peltier heating plate 106 affords the ability to measure, for example, fluid viscoelastic properties as a function of temperature with a fine degree of temperature control. In addition, detector 114 is provided to detect a light signal. For example detector 114 can detect light from a transmitted light beam emitted from light source 104 that passes through Peltier plate 106, fluid sample 103 and optical plate 108, as described in detail below. Light source 104 can be configured to provide, for example, a polarized light beam that can be used to measure fluid sample properties such as birefringence and dichroism. Light source 104 can be configured to supply a narrow beam of light, such as laser beam. Such a beam of light can penetrate through fluid sample 103 and optical plate 108 in a small region of optical plate 108 that lies underneath detector 114, such that a substantial portion of the transmitted beam can be detected by detector 114. Accordingly, system 100 provides a method to accurately measure the sample temperature dependence of fluid sample optical properties, while at the same time collecting viscoelastic information (embodiments of the present invention such as system 100, that are configured to make a plurality of different measurements are also termed "multi-measurement systems" and "optical rheometers").

FIGS. 2a and 2b depict side cross-sectional and top views, respectively, of a multimeasurement system 200 arranged in accordance with another embodiment of the present invention. Laser 204 acts as a light source to probe optical properties of fluid 103. Incident beam 206 is emitted from laser 204 at a substantially normal angle to the top and bottom surfaces 208, 210 of Peltier heating plate 106. Channel 212 extends from top surface 208 to bottom surface 210 along a longitudinal axis substantially parallel to beam 206, so that the intensity of beam 206 exiting Peltier heating plate 106 at surface 208 is a substantial fraction of the beam intensity at surface 210, preferably greater than about 50%. Fluid sample 103 and optical plate 108 can attenuate beam 206, so that attenuated beam 214 emerging from the top of optical plate 108 is reduced in intensity with respect to beam 206. However, beam 214 still provides a significant intensity at detector 114. Optical measurements of fluid sample 103 can be performed while Peltier heating plate 106 heats fluid sample 103. Thus, the temperature dependence of optical properties of fluid sample 103 can be recorded by recording the Peltier plate temperature while optical measurements are recorded at detector 114. Additionally, known viscoelastic measurements of fluid sample 103 can be performed at the same time, or at the same fluid sample temperature at which the optical measurements are performed. For example, an accelerometer or other device (not shown) could be used to measure the response of optical plate under a rotational applied force. In one particular example, at a first temperature, a rotational movement, such as a full rotation or an oscillation could be provided to optical plate 108. During the rotation or oscillation of optical plate 108, using detector 114, the optical properties of fluid sample 103 are measured based on detected beam 214. At the same time, a viscoelastic response of fluid sample 103 due to the rotation of optical plate 108 is measured using an accelerometer (not shown). Peltier heating plate 106 heats or cools the fluid sample to one or more additional temperatures, at which additional optical property and viscoelastic property measurements are made using detector 114 and an accelerometer. In this manner, fluid sample optical measurements can be correlated with viscoelastic measurements over a range of temperatures. In a preferred embodiment, the temperature range accessible for fluid sample measurements is about from −40 C. to about 200° C.

The system geometry depicted in FIGS. 2a and 2b provides a convenient means to perform sensitive optical measurements of a fluid sample, including birefringence and dichroism. Because incident beam 206 impinges on fluid sample 103 at near normal incidence, additional optical elements used for such measurements, including polarizers, analyzers, photoelastic modulators, and quarter wave plates, can be conveniently arranged within the beam path.

Figures 3A, 3B:
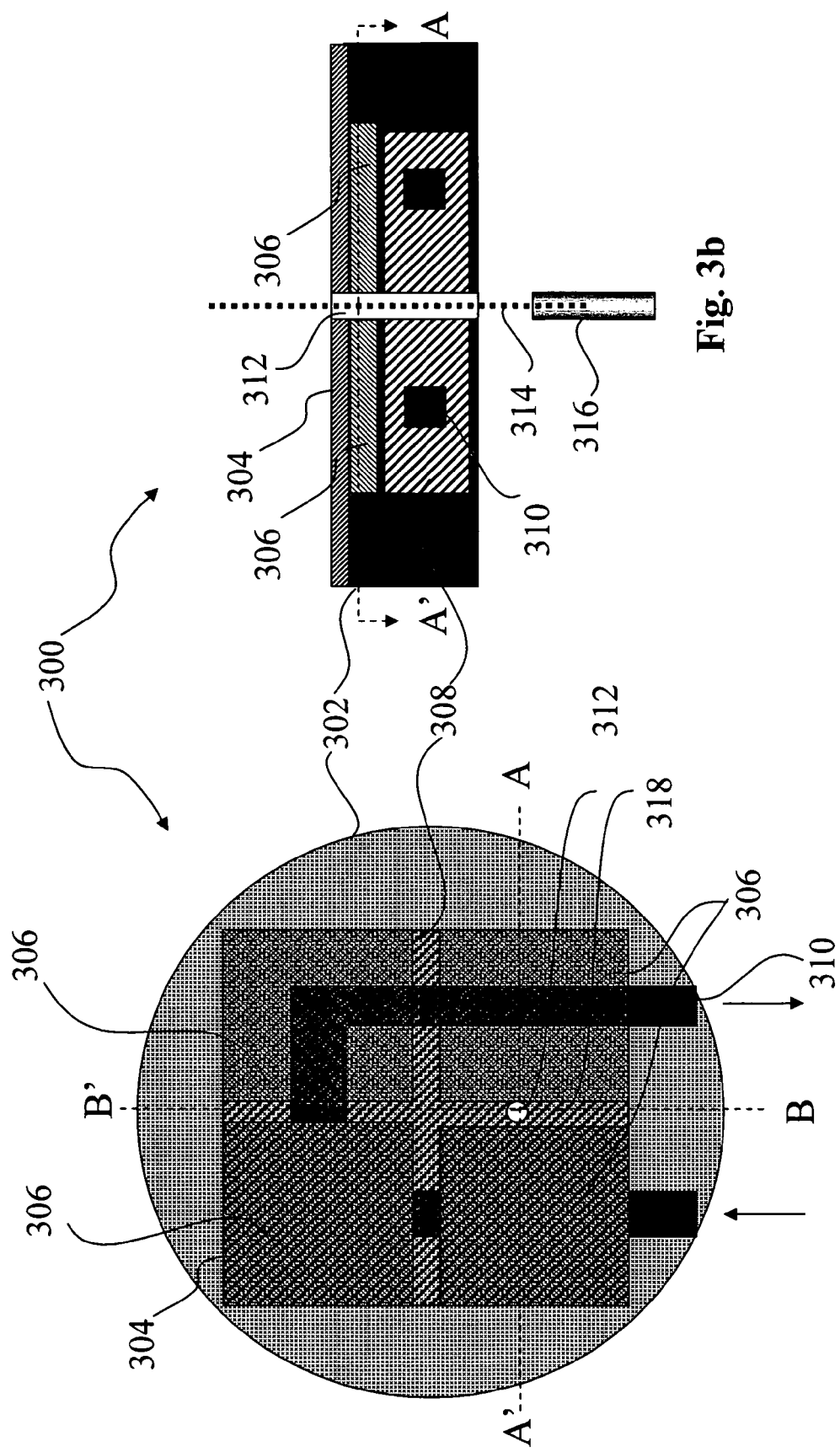

FIGS. 3a and 3b depict in a top view and cross-sectional side view, respectively, details of a Peltier heating plate 300, according to an embodiment of the present invention. Located within housing 302 are four Peltier heating elements 306 that are adjacent to water jacket 308. Peltier heating elements 306 can be electrically interconnected. When Peltier heating elements 306 heat up (or cool down), excess heat is dissipated (or supplied) through water jacket 308 that acts as a heat exchanger. Fluid channel 310 provides a path for cooling water (or other cooling fluid) to circulate through water jacket 308 so that heat can be removed. Surface heat distribution layer 304 is a highly heat conductive layer (a layer having high heat conductivity) that serves to create a uniform temperature on the top surface of Peltier heating plate 300. In one embodiment, layer 304 is a copper plate. In one embodiment, layer 304 is mated with a hard wear resistant layer (not shown). Optical channel region 312 permits laser beam 314 emitted from laser 316 to pass through Peltier heating plate 300. In the embodiment illustrated in FIGS. 3a and 3b, optical channel region is located so that it passes through border region 318 located between Peltier heating elements 306. In this manner, laser beam 314 can pass through Peltier heating plate 300 without significant disturbance to impinge on a fluid sample (not shown) disposed on layer 304, while at the same time Peltier heating elements 306 provide substantially uniform heating of the fluid sample on surface layer 304.

FIG. 3c depicts a cross-sectional view of Peltier heating plate 300 viewed along direction B-B' as indicated in FIG. 3a, according to one embodiment of the present invention. Transparent window 322 is disposed within optical channel region 312 to prevent fluid sample (not shown) from entering channel region 312 while allowing a light beam, such as laser beam 314 to pass through optical channel region 312 without substantial attenuation. Preferably, window 322 is comprised of a material whose thermal expansion coefficient is comparable to that of adjacent plate portions 304, 308. In this manner, thermal stresses that can arise from differential thermal expansion during heating or cooling when there is a large mismatch in thermal expansion coefficients between window 322 and water jacket 308 be reduced. In one embodiment of the present invention, a low elastic modulus sleeve material (not shown) is provided to surround window 322 and reduce any stress effect of thermal expansion coefficient mismatch between window 322 and plate portions 308, 304. In a further preferred embodiment of the present invention, window 322 comprises a material that has a low stress-birefringence ratio so that any stresses arising in window 322 during heating or cooling induce a minimal amount of birefringence in window 322, thus preventing spurious birefringence signals that could interfere with birefringence measurements of fluid sample 103.

Also included in heat distribution layer 304 is an embedded thermocouple 324 to accurately measure the surface temperature of the heating plate, so that fluid sample temperature can be accurately determined. Because the Peltier heating elements arrangement illustrated in FIGS. 3a-c provides a high degree of temperature control, the fluid sample temperature for a fluid in contact with surface region 304 can be controlled and measured to within about 0.1-0.01° C.

Figure 4:
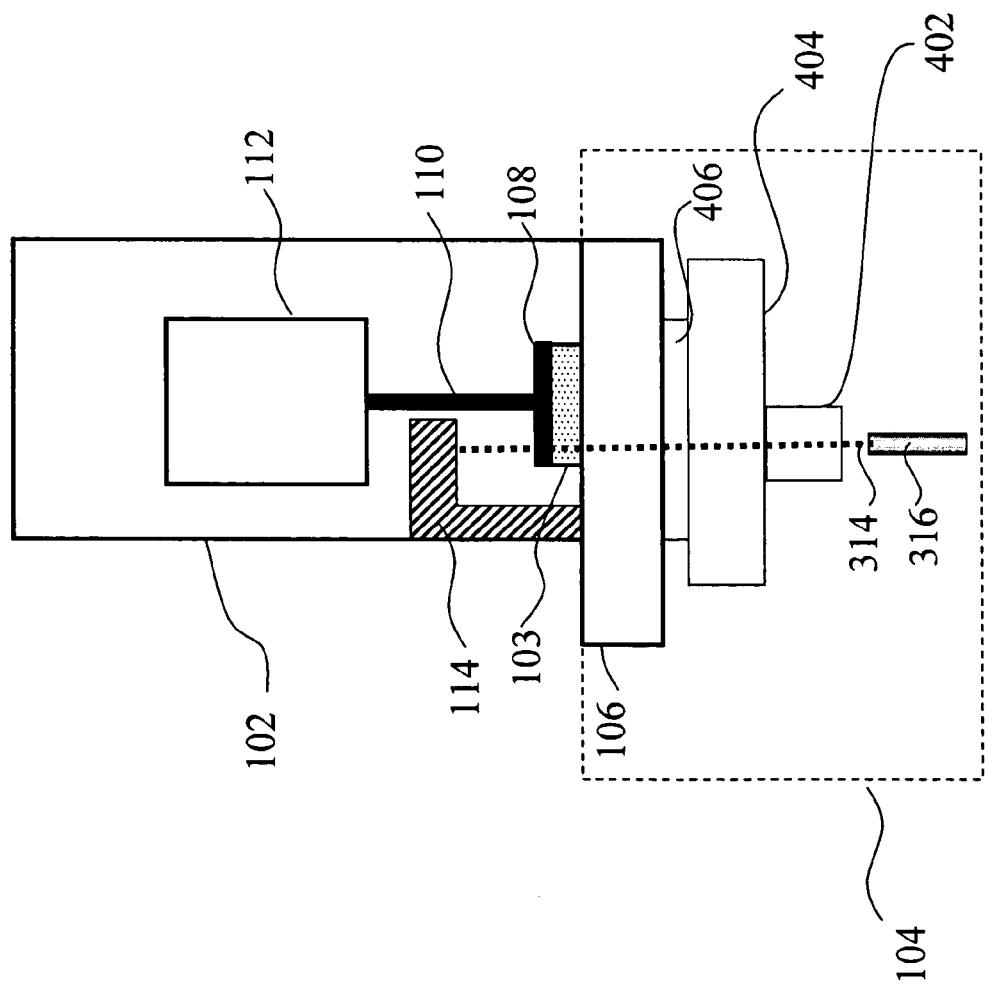
FIG. 4 depicts details of a light source arranged according to another embodiment of the present invention.

FIG. 4 depicts details of light source 104 according to another embodiment of the present invention. Light source 104 includes laser 316, polarizer 402, photoelastic modulator (PEM) 404, and quarter wave plate 406. Light source 104 thus provides an arrangement to conduct birefringence experiments by manipulating beam 314 using polarizer 402, PEM 404 and quarter wave plate 406, and measuring a transmitted beam at detector 114 after it passes through an analyzer (not shown). For example, a PEM contained in module 104 can be used to receive a polarized beam passing out of polarizer 402 and to pass a modulated beam that contains one component of the polarized beam that is retarded with respect to a second component. After interacting with optical plate 108 and fluid sample 103, polarized components of the emitted beam (not shown) can be passed through an analyzer and exit as an analyzed beam recorded by detector 114. The analyzed beam can provide information useful in determining birefringence, dichroism and other related fluid sample properties that can be studied using polarized beams.

In sum, the combination of a Peltier plate arrangement having uniform heating over a plate surface and an accommodation of an optical probe (light beam) channel within a Peltier heating plate (PHP), provides unique measurement capabilities to the embodiments of the present invention disclosed above. Many details of fluid sample behavior can be conveniently probed. For example, the crystallization behavior of fluid polymers that crystallize upon a change in temperature can be studied by carefully controlling and measuring the PHP temperature while simultaneously recording sample optical properties using a light beam probe. In one example, optical properties that are especially sensitive to polymer crystallization such as birefringence can be studied.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. For example, the present invention encompasses many other arrangements of individual Peltier elements that provide uniform heating across a plate surface and accommodate an optical channel for an optical probe. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process, should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. An optical rheometer system, comprising:
    a rheometer chamber configured to contain a fluid sample;
    a light source to provide a light beam incident on the fluid sample;
    a Peltier heating plate having a channel region configured to substantially transmit the light beam through the Peltier heating plate such that light of the light beam leaving the channel region at an exit point passes through the fluid sample;
    a rotating optical plate having a surface substantially opposing a first surface of the Peltier heating plate in a region proximate to the exit point, the rotating optical plate configured to transmit the light beam; and
    a detector for measuring transmitted light passing through the rotating optical plate.

2. The optical rheometer system of claim 1, wherein the light source comprises a narrow beam.

3. The optical rheometer system of claim 1, wherein the light source comprises:
    a laser source that emits a laser beam;
    a polarizer configured to polarize the emitted laser beam;
    a photoelastic multiplier that modulates the polarized emitted beam; and
    a quarter wave plate that optimizes the duty cycle of the polarized emitted beam.

4. The system of claim 1, the Peltier heating plate comprising:
    a hard metallic wear resistant surface;
    a highly heat conductive layer for even distribution of heat in the heating plate;
    an array of Peltier heating elements separated from each other by a boundary region; and
    a water jacket heat exchanger to remove excess heat from the Peltier heating plate, wherein the channel region resides within the boundary region.

5. The optical rheometer system of claim 4, wherein the array of Peltier elements comprises a two by two array of electrically interconnected elements all substantially the same size and shape.

6. The optical rheometer system of claim 4, the Peltier heating plate further comprising a transparent window disposed within the channel and having an outer surface substantially flush with the wear resistant surface of the Peltier heating plate, wherein the transparent window is configured to preclude sample fluid from entering the channel region.

7. The optical rheometer system of claim 6, further comprising a low elastic modulus sleeve configured to minimize thermal expansion stress between the transparent window and water jacket.

8. The optical rheometer of claim 6, wherein the transparent window comprises a material having low stress birefringence.

9. The optical rheometer of claim 6, wherein the Peltier heating plate is configured to impart to a fluid sample a range of temperatures from about −40° C. to about 200° C.

10. A system for performing multiple measurements on a fluid sample, comprising:
    a chamber configured to contain a fluid sample;
    a light source to provide a light beam incident on the fluid sample;
    a Peltier heating plate having a channel region configured to substantially transmit the light beam through the Peltier heating plate such that light of the light beam leaving the channel region at an exit point passes through the fluid sample;
    a rotating optical plate having a plate surface substantially opposing a first surface of the Peltier heating plate in a region proximate to the exit point, the rotating optical plate configured to transmit the light beam;

a motion-sensing device configured to measure a response of the rotating optical plate under a rotational applied force; and an optical detector for measuring properties of the light transmitted through the rotating optical plate, wherein the system is configured to provide simultaneous optical and rheometric measurements of the fluid during heating or cooling of the fluid.

11. The system of claim 10, wherein the light source comprises:

a laser source that emits a laser beam;

a polarizer configured to polarize the emitted laser beam;

a photoelastic multiplier that modulates the polarized emitted beam; and a quarter wave plate that optimizes the duty cycle of the polarized emitted beam.

12. An optical rheometer system, comprising:

a rheometer chamber configured to contain a fluid sample;

a rotating optical plate for imparting a stress or strain in the fluid sample;

a heating means having a first surface in contact with the fluid sample and disposed opposite the rotating optical plate, the heating means comprising a channel region configured to transmit a readily measurable portion of a light beam incident on the second surface as a transmitted light beam that passes through the heating means, the fluid sample and rotating optical;

a light source means configured to provide a light beam incident on a second surface of the heating means opposite to the first surface; and a detector for measuring the transmitted light beam.

13. The optical rheometer system of claim 12, wherein the heating means comprises a Peltier heating plate that further comprises:

a hard metallic wear resistant surface;

a highly heat conductive layer for even distribution of heat in the heating plate;

an array of Peltier heating elements separated from each other by a boundary region; and a water jacket heat exchanger to remove excess heat from the Peltier heating plate, wherein the channel region resides within the boundary region.

14. The optical rheometer system of claim 13, the Peltier heating plate further comprising a transparent window disposed within the channel and having an outer surface substantially flush with the wear resistant surface of the Peltier heating plate, wherein the transparent window is configured to preclude sample fluid from entering the channel region.

15. The optical rheometer system of claim 13, wherein the array of Peltier elements comprises a two by two array of electrically interconnected elements all substantially the same size and shape.

16. The optical rheometer system of claim 13, wherein the light source means comprises:

a laser source that emits a laser beam;

a polarizer configured to polarize the emitted laser beam;

a photoelastic multiplier that modulates the polarized emitted beam; and a quarter wave plate that optimizes the duty cycle of the polarized emitted beam.

17. A method of in-situ sample characterization as a function of temperature, comprising:

providing a heating plate configured with a channel extending from a first surface to a second surface of the heating plate, the channel configured to pass from the first surface a readily measurable portion of light that is incident on the second surface;

providing a rotating optical plate;

providing a sample fluid in contact with the first surface of the heating plate and in contact with the rotating optical plate;

providing a light source incident on the second surface in a region of the heating plate containing the channel;

applying a rotational movement to the rotating optical plate at a plurality of temperatures;

measuring, at the plurality of temperatures, a transmitted light signal corresponding to light transmitted through the channel, the sample fluid, and the rotating optical plate;

measuring, at the plurality of temperatures, a viscoelastic response signal of the sample fluid in response to the first rotational movement; and correlating, as a function of temperature, the measured transmitted light signal with the measured viscoelastic response signal for each of the plurality of temperatures.

18. The method of claim 17, wherein the light source is a laser beam.

19. The method of claim 17, wherein the heating plate comprises a Peltier heating plate comprising a plurality of heating elements, wherein the heating plate is configured to impart to a fluid sample a range of temperatures from about −40° C. to about 200° C.

20. The method of claim 19, wherein an accuracy of temperature measurement is about 0.1° C. to about 0.01° C.

\* \* \* \* \*